United States Patent
Bays et al.

(10) Patent No.: US 6,364,874 B1
(45) Date of Patent: *Apr. 2, 2002

(54) DEVICE FOR IRRADIATING INTERNAL CAVITIES OF THE BODY

(75) Inventors: Roland Bays, Romont; Alain Woodtli, Saint-Aubin; Georges Wagnieres, Morges; Hubert Van Den Bergh, Goumoens-la-Ville, all of (CH)

(73) Assignee: Medlight S.A., Ecublens (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/297,386
(22) PCT Filed: Aug. 28, 1998
(86) PCT No.: PCT/CH98/00370
    § 371 Date: Apr. 30, 1999
    § 102(e) Date: Apr. 30, 1999
(87) PCT Pub. No.: WO99/11322
    PCT Pub. Date: Mar. 11, 1999

(30) Foreign Application Priority Data

Sep. 4, 1997 (FR) .............................................. 97 11253

(51) Int. Cl.[7] .............................................. A61B 18/18
(52) U.S. Cl. .............................. 606/15; 606/13; 606/16; 606/78; 607/88; 607/89; 607/92
(58) Field of Search ....................... 607/92; 606/13–15, 606/16, 76, 78; 128/898

(56) References Cited

U.S. PATENT DOCUMENTS

| | | | | |
|---|---|---|---|---|
| 4,968,314 A | * | 11/1990 | Micheals | 606/7 |
| 5,019,075 A | * | 5/1991 | Spears et al. | 606/3 |
| 5,209,748 A | * | 5/1993 | Daikuzono | 606/16 |
| 5,219,346 A | * | 6/1993 | Wagnieres et al. | 606/15 |
| 5,246,421 A | * | 9/1993 | Saab | 604/96 |
| 5,344,419 A | * | 9/1994 | Spears | 606/15 |
| 5,409,483 A | * | 4/1995 | Campbell et al. | 606/15 |
| 5,415,654 A | * | 5/1995 | Daikuzono | 606/15 |
| 5,441,497 A | * | 8/1995 | Narciso, Jr. | 606/15 |
| 5,637,074 A | * | 6/1997 | Andino et al. | 600/29 |
| 5,645,562 A | * | 7/1997 | Haan et al. | 606/194 |
| 5,688,263 A | * | 11/1997 | Hauptmann et al. | 606/13 |
| 5,709,653 A | * | 1/1998 | Leone | 604/20 |
| 5,797,868 A | * | 8/1998 | Leone | 604/21 |
| 5,799,661 A | * | 9/1998 | Body et al. | 128/898 |
| 5,836,591 A | * | 11/1998 | Rosenbluth et al. | 606/108 |
| 5,840,008 A | * | 11/1998 | Klein et al. | 606/3 |

(List continued on next page.)

FOREIGN PATENT DOCUMENTS

| | | |
|---|---|---|
| EP | 0 292 695 | 11/1988 |
| EP | 0 411 132 | 2/1991 |
| EP | 0 673 627 | 9/1995 |
| FR | 2 600 205 | 12/1987 |
| WO | WO 95 08949 A | 4/1995 |

*Primary Examiner*—Linda C. M. Dvorak
*Assistant Examiner*—Ahmed Farah
(74) *Attorney, Agent, or Firm*—Nixon & Vanderhye P.C.

(57) ABSTRACT

A device for the irradiation of internal cavities of the body includes a flexible catheter, made of a transparent material, containing a fiber optic of which the section at one end is designed to radially diffuse light coming from a source arranged at the other end. An inflatable balloon fixed to one end of the catheter surrounds the diffusing section of the fiber optic. The balloon is made of an elastomeric material that diffuses the light and is prefabricated by molding based on the shape of the cavity to be treated. The balloon presses against the cavity wall and, with the thickness of its surfaces remaining constant after inflation, the pressure needed for inflation is low and cannot damage the cavity tissues.

19 Claims, 2 Drawing Sheets

U.S. PATENT DOCUMENTS

Figure 1:
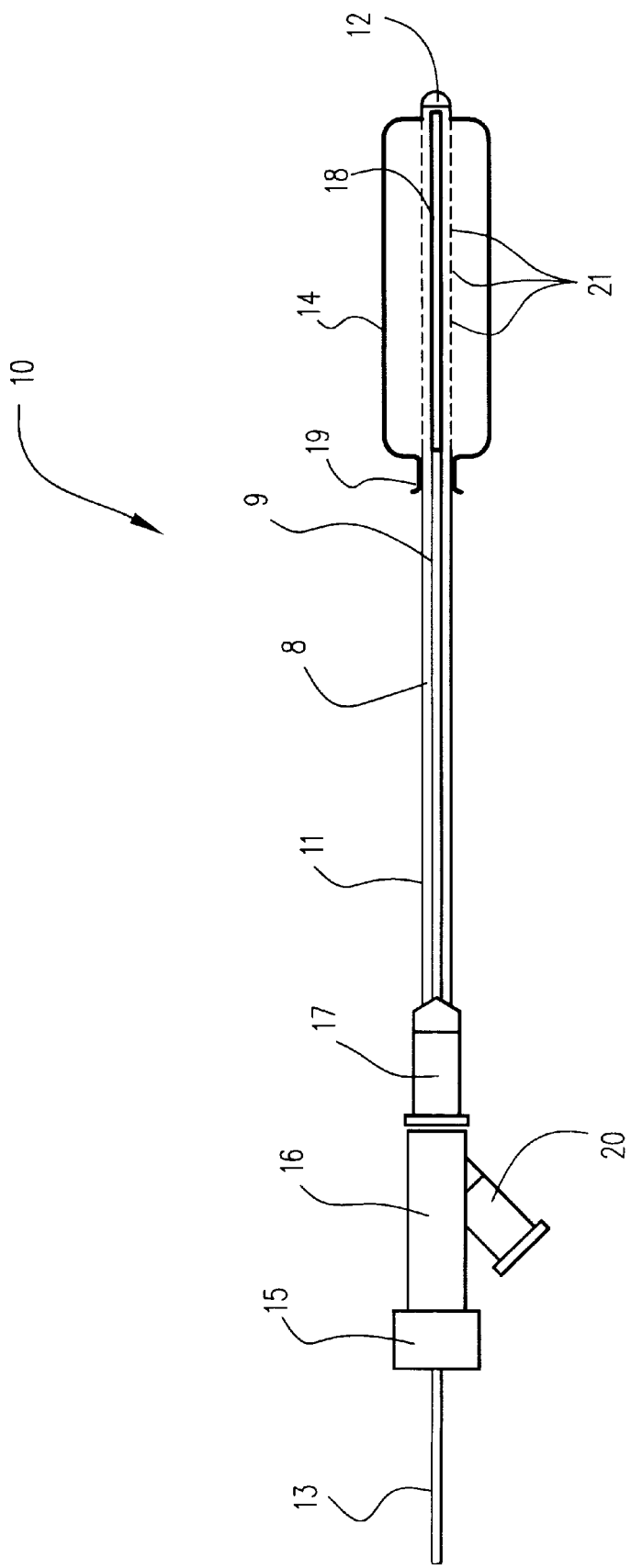

| | | | |
|---|---|---|---|
| 5,855,563 A | * 1/1999 | Kaplan et al. | 604/49 |
| 5,879,499 A | * 3/1999 | Corvi | 156/175 |
| 5,964,751 A | * 10/1999 | Amplatz et al. | 606/15 |
| 5,997,570 A | * 12/1999 | Ligtenberg et al. | 607/92 |
| 6,086,558 A | * 7/2000 | Brower et al. | 604/96 |
| 6,143,016 A | * 11/2000 | Bleam et al. | 606/198 |
| 6,146,409 A | * 11/2000 | Overholt et al. | 607/88 |

* cited by examiner

DEVICE FOR IRRADIATING INTERNAL CAVITIES OF THE BODY

This application is a 371 of PCT/CH98/00370, filed Aug. 28, 1998.

TECHNICAL DOMAIN

The current invention is an appliance for the irradiation of internal cavities of the body, in particular for the treatment of specific diseases using photodynamic therapy. This appliance is comprised of a flexible catheter, made of transparent material containing a fiber optic with the section at its tip being used to radially diffuse light from a source at the other end of this fiber, and an inflatable small balloon in elastomeric material which diffuses the light and which is fixed to the extremity of the catheter and surrounds the diffusing section of the optic fiber.

1. Previous Technique

In the treatment of certain cancerous lesions in human body cavities, such as the bronchii, the esophagus or the uterus, photodynamic therapy is being used with increasing frequency. This involves irradiation of the tumor using diffused light. This irradiation is conducted using appliances comprised of a catheter containing a fiber optic linked to a laser light source which can be introduced into the biopsy channel of a classic endoscope. In order to obtain light diffusion that is as homogeneous as possible and to prevent damage to the cavity walls, the tip of the catheter introduced into the cavity is surrounded by a balloon which, once it is in place, is inflated to support the cavity walls to be treated.

In the appliances currently used, in particular the one described in publication DE 39 09 843, when dealing with an irregular cavity, a layer of material with diffusing properties is applied to the cavity walls in order to obtain homogeneity in the light diffused. An elastic envelope can similarly be used. The vaporization of the diffusing layer is a delicate operation and, if an inflatable elastic envelope is used in this type of cavity, firstly the inflating pressure has to be sufficiently high for the envelope to press against the cavity wall which results in high and differentiated pressure constraints on the cavity walls and risks modifying tissue vascularization and, secondly, differences in thickness are created in the envelope wall which results in irregular light transmission.

2. Description of the Invention

The aim of the current invention is to eliminate these drawbacks by providing an appliance in which the elastic envelope, or small balloon, presses well against the surface to be treated and thus applies uniform pressure to the cavity walls, while the thickness of the balloon walls remain constant after inflation. In addition, the pressure needed for this inflation is weak, which means that the resultant pressure applied by the balloon on the cavity tissues to be treated is likewise weak and there is no risk of damage. In this way, there is a homogeneous back-scattering of the diffused light in all shapes of cavity to be treated while being careful with these cavity walls.

The appliance described at the beginning is characterized by the balloon which is fabricated using a mold shaped roughly like that of the cavity to be treated in order to take on its shape and to apply uniform pressure on the cavity walls.

Ideally, the balloon could be made by using a mold taken from the specific impression of the cavity to be treated.

In all its design versions, the balloon includes a neck designed to be slipped onto the tip of the catheter surrounding the diffusing section of the fiber optic and, as a result, the longitudinal axis of the fiber optic's diffusing section is identical to the symmetrical axis of the balloon.

Preferably, the fiber optic is sheathed in a protective casing.

According to the preferred design type, the catheter includes, at the opposite extremity to that covered by the balloon, an axial aperture designed to receive the fiber optic and a radial aperture designed for the introduction of the means to inflate the balloon in the space bounded by the interior wall of the catheter and the protective casing sheathing the fiber optic.

The balloon can be inflated either with air or a sterile liquid, for example water.

In order to diffuse the means of inflation within the balloon, the tip of the catheter covered by the balloon has radial apertures, spaced at regular intervals and arranged around its periphery.

In all its design versions, the balloon is designed to be inflated after introduction into the cavity to be treated.

As an advantage, it can include the means to control the pressure applied by the balloon on the walls of the cavity to be treated.

CONCISE DESCRIPTION OF THE DRAWINGS

Figure 2:
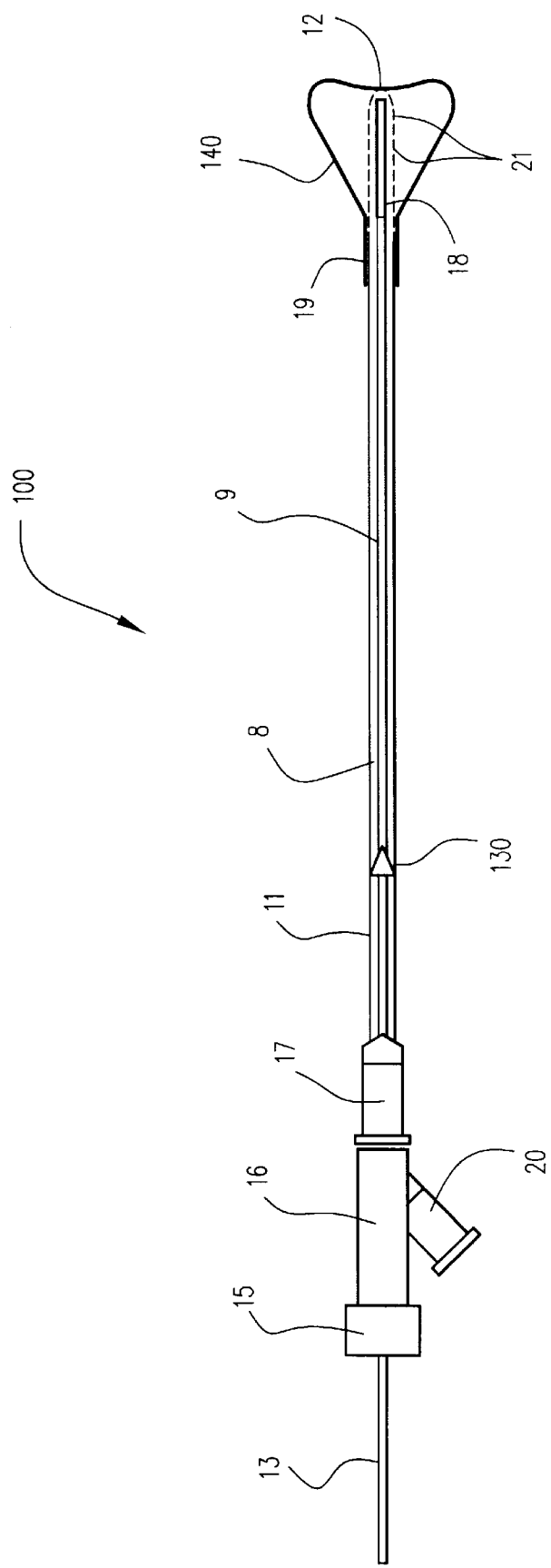

The current invention will be better understood in reference to the description of preferred design examples and the drawings appended in which:

FIG. 1 represents an initial implementation of the appliance according to the invention for the irradiations of a patient's bronchi and FIG. 2 represents a second implementation of the appliance designed to irradiate a patients uterus.

BEST METHODS OF PRODUCING THE INVENTION

With reference to FIG. 1, appliance (10), designed to be introduced into a patient's bronchi, is comprised of a catheter (11) made of a flexible, transparent material and closed at one (12) of its extremities, a fiber optic (13) positioned in this catheter and an inflatable balloon (14) attached to the extremity (12) of the catheter (11). The dimensions of the appliance (10) are such that it can be inserted in the biopsy channel of a classic endoscope (not shown) intended for the examination of organs in the human body.

The fiber optic (13), of which the diameter is less than that of the catheter (11) is sheathed in a protective casing (9) and inserted into the catheter through an axial aperture (15) of a tip (16) integral with the other end (17) of the catheter until it comes into contact with extremity (12) thereby defining a space (8) between the external wall of the casing (9) and the internal wall of the catheter (11). This fiber optic (13) which is designed to conduct light issuing from a source (not shown) to the extremity (12) of the catheter, is fitted, at the end introduced into the catheter, with a section (18) that is characterized by being able to radially diffuse light transmitted by the fiber optic.

The balloon (14), which is intended to homogenize the light diffused in the cavity to be treated by the section (18) of the fiber optic (13) so that irradiation of this cavity, in this example the bronchi, is done uniformly, is an inflatable balloon which, once inflated, is to press against the cavity wall to be treated. For this purpose, it is produced in an elastomeric material that can be shaped, such as latex or silicone which, in this application is loaded with particles of a diffusive material such as titanium dioxide to improve the diffusion properties of the balloon. This balloon is introduced folded, on the catheter's extremity (12) so that it surrounds the diffusing section (18). For this purpose, it has, at one of its extremities, a neck (29) which has the same diameter as that of the catheter's (11) external diameter in order to ensure that the diffusing section (18) of the fiber optic (13) remains centered with reference to the balloon (14). It is bonded to the catheter and by a neck (19) ligature to the external surface of the catheter (11).

In order for the light to irradiate the cavity in a uniform way through the inflatable balloon, the latter must take on the shape of the cavity while still maintaining a constant wall thickness so that all the points to be irradiated receive the same amount of light. It is not possible to achieve this with balloons of the standard elongated or cylindrical shapes. As a result, the balloon (14) of the invention is created exactly to the shape of the cavity, in this example an elongated cylinder, into which it is to be introduced. In order to obtain this, a known method is used to make a molding of a specific impression of the cavity to be treated.

The balloon, which is introduced folded into the cavity, is subsequently inflated by means of air or a sterile liquid such as water under pressure introduced in the space (8) between the fiber optic (13) and the internal surface of the catheter through a radial aperture (20) made in the tip (16). This air or this liquid is injected into the balloon (14) via radial apertures (21) which are spaced at regular intervals and arranged around the periphery of the section at the catheter's extremity which is inside the balloon. The use of a liquid as a means of inflation allows the diffusing section (18) of the fiber optic to be cooled if necessary.

Given that the balloon is shaped like the cavity, the pressure needed for inflating it is weak and this eliminates problems with vascular condition changes in the tissues concerned due to excessive pressure applied to the cavity walls, which would produce variations in the efficacy of the therapy.

In order to ensure that the appliance is leakproof, apertures (15 and 20) of the tip (16) have, respectively, a closure in the form of an O-ring joint for the axial aperture (15) and a stopper integral with a valve (not shown) for the aperture (21), with said valve allowing regulation of the pressure under which the means of inflation for the balloon is introduced and thus controlling the resultant pressure applied by the balloon to the tissues.

FIG. 2 illustrates an appliance (100) intended to treat the walls of a patient's uterus. It is comprised of identical elements to those described in reference to FIG. 1 and carries the same reference, with only the balloon (140) being different. This balloon (140) which is shaped like a uterus is obtained from shaping in a mold, for example in aluminum, created from an impression of the uterus to be treated. The flexibility of the balloon allows the appliance to adapt to the uterus' real dimensions which can vary between two patients and, as a result, it is not necessary to create a balloon for each patient to be treated.

In this design, with the balloon having a specific shape, it is necessary to provide for an orientation mark (130) on the catheter (11) so that on introduction of the appliance into the body, the balloon (140) is correctly positioned in relation to the uterus and that it presses well against the wall to be treated when inflated.

In other designs, the single fiber optic could be replaced by several fibre optics dependent on the amount of illumination required.

What is claimed is:

1. A device for the irradiation of internal cavities of the body, in particular for the treatment of certain diseases using photodynamic therapy, comprising a flexible catheter made of a transparent material, closed at one of its extremities, containing a fiber optic of which the section at its extremity is arranged to radially diffuse light coming from a source provided at the other end of the fiber optic and an inflatable balloon made of an elastomeric material containing particles of a diffusive material so to be able to diffuse light, fixed to one extremity of the catheter in such a way as to surround the diffusing section of the fiber optic, wherein the balloon is pre-molded to take on, when inflated, the approximate shape of the cavity to be treated, and wherein the balloon, when inflated during use of the device, takes on that shape and applies uniform pressure to the walls of that cavity.

2. The device according to claim 1, wherein the shape of the balloon obtained by molding is identical to that of a specific impression of the cavity to be treated.

3. The device according to claim 1, wherein the balloon has a neck designed to be fitted to the extremity of the catheter surrounding the diffusing section of the fiber optic.

4. The device according to claim 3, wherein the longitudinal axis of the diffusing section of the fiber optic is identical to the symmetrical axis of the balloon.

5. The device according to claim 1, wherein the fiber optic is sheathed in a protective casing.

6. The device according to claim 1, wherein the catheter includes, at the opposite extremity to that covered by the balloon, an axial aperture designed to receive the fiber optic and a radial aperture designed for the introduction of means to inflate the balloon in the space bounded by the interior wall of the catheter and a protective casing sheathing the fiber optic.

7. The device according to claim 6, wherein the means of inflation for the balloon is air.

8. The device according to claim 6, wherein the means of inflation for the balloon is a sterile liquid.

9. The device according to claim 6, wherein the tip of the catheter surrounded by the balloon includes radial apertures spaced at regular intervals to diffuse the means of inflating the balloon.

10. The device according to claim 1, wherein the balloon is designed to be inflated after it has been introduced into the cavity to be treated.

11. The device according to claim 1, further comprising means of controlling pressure applied by the balloon on the cavity walls to be treated.

12. The appliance according to claim 1, wherein the particles of a diffusive material are titanium dioxide.

13. A device for treating an internal cavity of the body by irradiation comprising:
a flexible catheter, made of a transparent material and closed at one of its ends, containing a fiber optic having a diffusing section at one end thereof that is arranged to radially diffuse light coming from a source provided at the other end thereof; and
an inflatable balloon comprised of a light-diffusive, elastomeric material and fixed to the closed end of the catheter so as to surround the diffusing section of the fiber optic, wherein the balloon is pre-molded to take on, when inflated, the approximate shape of the body cavity to be treated, and wherein the balloon, when inflated during use of the device, takes on that shape and applies uniform pressure to the walls of that body cavity.

14. The device according to claim 13, wherein the light-diffusive, elastomeric material comprises titanium dioxide.

15. The device according to claim 13, wherein a longitudinal axis of the diffusing section of the fiber optic is aligned with an axis of symmetry of the balloon.

16. The device according to claim 13, wherein the fiber optic is sheathed in a protective casing.

17. The device according to claim 13, wherein the balloon is inflated with air.

18. The device according to claim 13, wherein the balloon is inflated with a sterile liquid.

19. The device according to claim 13, wherein the flexible catheter includes indicia usable to correctly position the balloon in relation to the body cavity to be treated.

\* \* \* \* \*